(12) United States Patent
Oikawa et al.

(10) Patent No.: US 11,406,600 B2
(45) Date of Patent: Aug. 9, 2022

(54) ANHYDROUS DASATINIB-CONTAINING PREPARATION

(71) Applicant: SAWAI PHARMACEUTICAL CO., LTD., Osaka (JP)

(72) Inventors: Michinori Oikawa, Osaka (JP);
Hiroyuki Yamamoto, Osaka (JP);
Hiroaki Kikuoka, Osaka (JP)

(73) Assignee: SAWAI PHARMACEUTICAL CO., LTD., Osaka (JP)

( * ) Notice: Subject to any disclaimer, the term of this patent is extended or adjusted under 35 U.S.C. 154(b) by 18 days.

(21) Appl. No.: 16/879,408

(22) Filed: May 20, 2020

(65) Prior Publication Data

US 2020/0281859 A1    Sep. 10, 2020

Related U.S. Application Data

(63) Continuation of application No. PCT/JP2018/042968, filed on Nov. 21, 2018.

(30) Foreign Application Priority Data

Nov. 22, 2017   (JP) .............................. JP2017-224570

(51) Int. Cl.
*A61K 9/28* (2006.01)
*A61K 31/506* (2006.01)

(52) U.S. Cl.
CPC .......... *A61K 9/2813* (2013.01); *A61K 31/506* (2013.01)

(58) Field of Classification Search
CPC ................................. A61K 9/28; A61K 31/506
See application file for complete search history.

(56) References Cited

U.S. PATENT DOCUMENTS

| | | | |
|---|---|---|---|
| 2006/0251723 A1 | 11/2006 | Gao et al. | |
| 2008/0200536 A1 | 8/2008 | Moon et al. | |
| 2009/0041843 A1 | 2/2009 | Kozaki et al. | |
| 2009/0105265 A1 | 4/2009 | Kamali et al. | |
| 2009/0118297 A1 | 5/2009 | Simo et al. | |
| 2010/0284987 A1 | 11/2010 | Diguet et al. | |
| 2011/0245301 A1 | 10/2011 | Park et al. | |
| 2014/0234417 A1 | 8/2014 | Inoue | |
| 2016/0220494 A1* | 8/2016 | Stroyer | A61K 9/1652 |

FOREIGN PATENT DOCUMENTS

| | | |
|---|---|---|
| EP | 2359813 A1 | 8/2011 |
| JP | 2003-104888 A | 4/2003 |
| JP | 2004-210702 A | 7/2004 |
| JP | 2004-277415 A | 10/2004 |
| JP | 2005-187339 A | 7/2005 |
| JP | 2006-306754 A | 11/2006 |
| JP | 2007-126407 A | 5/2007 |
| JP | 2008-133231 A | 6/2008 |
| JP | 2008-540440 A | 11/2008 |
| JP | 2009-504728 A | 2/2009 |
| JP | 2009-519934 A | 5/2009 |
| JP | 2010-533667 A | 10/2010 |
| JP | 2010-539156 A | 12/2010 |
| JP | 2012-515768 A | 7/2012 |
| JP | 2012-246325 A | 12/2012 |
| JP | 2013-518860 A | 5/2013 |
| JP | 2015-178482 A | 10/2015 |
| JP | 2015-221782 A | 12/2015 |
| JP | 2016-135782 A | 7/2016 |
| JP | 6081763 B2 | 2/2017 |
| WO | 2008/114859 A1 | 9/2008 |
| WO | 2013/054872 A1 | 4/2013 |
| WO | 2017/103057 A1 | 6/2017 |
| WO | WO 2017/103057 * | 6/2017 |

OTHER PUBLICATIONS

SPRYCEL Tablet, Pharmaceutical Interview Form (Aug. 2016) (Revised 11th Edition) along with a partial English translation, cited in the Specification.
International Search Report issued in corresponding International Patent Application No. PCT/JP2018/042968 dated Feb. 5, 2019, along with an English translation.
Written Opinion issued in corresponding International Patent Application No. PCT/JP2018/042968 dated Feb. 5, 2019.
Anonymous, "Process for preparing dasatinib formulations," IP.com Journal, May 7, 2013 IPCOM000227417D, p. 1.
An English translation of Written Opinion issued in corresponding International Patent Application No. PCT/JP2018/042968 dated Feb. 5, 2019.
Office Action issued for corresponding Japanese Patent Application No. 2017-224570 dated Aug. 17, 2021, along with an English machine translation.
Notice of Written Submission of Information dated Nov. 2, 2021, including Written Submission of Information filed by a third party against Japanese Patent Application No. 2017-224570 corresponding to a foreign priority application, along with an English machine translation.
Notice of Written Submission of Information dated Nov. 30, 2021, including Written Submission of Information filed by a third party against corresponding Japanese Patent Application. No. 2017-224570, along with an English machine translation.
Notice of Written Submission of Information dated Dec. 7, 2021, including Written Submission of Information filed by a third party against corresponding Japanese Patent Application No. 2017-224570, along with an English machine translation.

(Continued)

*Primary Examiner* — Shirley V Gembeh
(74) *Attorney, Agent, or Firm* — Hauptman Ham, LLP

(57) ABSTRACT

An anhydrous dasatinib-containing preparation comprising an anhydrous dasatinib and a titanium oxide or colorant or antioxidant is provided. In one embodiment, the anhydrous dasatinib-containing preparation improves photostability upon storage. The weight ratio of the titanium oxide per the anhydrous dasatinib may be more than 0 and 2 or less, or the weight ratio of the colorant per the anhydrous dasatinib may be more than 0 and 1 or less, or the weight ratio of the antioxidant per the anhydrous dasatinib may be more than 0 and 0.5 or less.

4 Claims, 5 Drawing Sheets

(56) References Cited

OTHER PUBLICATIONS

Hashida, "Formulation Design of Oral Dosage Forms", Yakugyo Jiho Co., Ltd., 1998, pp. 188-189, along with an English machine translation, cited in NPL No. 2.
Makino et al., "The mechanism of blackening of tablets in white film-coating", Yakuzaigaku, Journal of Pharmaceutical science and technology, Japan, 54(1), 1994, pp. 61-67, along with an English machine translation, cited in NPL No. 2.
Bechard et al., "Film coating: effect of titanium dioxide concentration and film thickness on the photostability of nifedipine", International Journal of Pharmaceutics, 87, 1992, pp. 133-139, cited in NPL No. 2.
Office Action dated Mar. 29, 2022 for corresponding Japanese Patent Application No. 2017-224570, along with an English machine translation (10 pages).
Tsuda et al., "Basic Course in Drug Development IX: Formulation Design Method (2)", 1st edition. Tokyo, Japan: Chijin Shokan Co., Ltd., 1971, pp. 328-346, along with a partial English machine translation (21 pages), cited in NPL No. 1.

\* cited by examiner

Fig. 1

| | Comparative example 3 | Example 1 | Example 2 | Example 3 | Example 4 | Example 5 | Example 6 | Example 7 | Example 8 | Example 9 |
|---|---|---|---|---|---|---|---|---|---|---|
| Titanium oxide (mg) | 0 | 0.3 | 0.6 | 0.9 | 0.15 | 0.3 | 0.45 | 0.225 | 0.45 | 0.675 |
| Weight ratio of titanium oxide per anhydrous dasatinib | 0 | 0.015 | 0.03 | 0.045 | 0.0075 | 0.015 | 0.0225 | 0.01125 | 0.0225 | 0.03375 |
| Total of FC part (mg) | 3.2 | 3.2 | 3.2 | 3.2 | 1.6 | 1.6 | 1.6 | 2.4 | 2.4 | 2.4 |
| ΔE value | 15.03 | 1.59 | 0.48 | 0.07 | 4.94 | 2.29 | 1.88 | 3.26 | 1.51 | 0.81 |
| Total related substances (%) | 0.32 | 0.27 | 0.26 | 0.25 | 0.3 | 0.29 | 0.27 | 0.29 | 0.27 | 0.26 |

Fig. 2

|  | Comparative example 4 | Example 10 | Example 11 | Example 12 | Example 13 |
|---|---|---|---|---|---|
| Titanium oxide (mg) | 0 | 0.4 | 0.8 | 2.4 | 4 |
| Weight ratio of titanium oxide per anhydrous dasatinib | 0 | 0.02 | 0.04 | 0.12 | 0.2 |
| ΔE value | 8.8 | 4.42 | 3.83 | 3.02 | 2.84 |
| Total related substances (%) | 0.77 | 0.4 | 0.49 | 0.44 | 0.31 |

Fig. 3

|  | Comparative example 3 | Example 14 | Example 15 |
|---|---|---|---|
| Red ferric oxide (mg) | 0 | 0.01 | 0.1 |
| Weight ratio of red ferric oxide per anhydrous dasatinib | 0 | 0.0005 | 0.005 |
| Total of FC part (mg) | 3.2 | 3.21 | 3.3 |
| ΔE value | 15.03 | 6.16 | 0.58 |
| Total related substances (%) | 0.32 | 0.2 | 0.19 |

Fig. 4

| | Comparative example 4 | Example 16 | Example 17 | Example 18 | Example 19 | Example 20 | Example 21 |
|---|---|---|---|---|---|---|---|
| Yellow ferric oxide (mg) | 0 | 0.4 | 0.8 | 1.6 | 0 | 0 | 0 |
| Red ferric oxide (mg) | 0 | 0 | 0 | 0 | 0.4 | 0.8 | 1.6 |
| Weight ratio of yellow ferric oxide per anhydrous dasatinib | 0 | 0.02 | 0.04 | 0.08 | - | - | - |
| Weight ratio of red ferric oxide per anhydrous dasatinib | - | - | - | - | 0.02 | 0.04 | 0.08 |
| ΔE value | 8.8 | 1.87 | 1.41 | 1.07 | 2.13 | 1.83 | 0.74 |
| Total related substances (%) | 0.77 | 0.67 | 0.41 | 0.38 | 0.67 | 0.52 | 0.48 |

Fig. 5

| | Comparative example 4 | Example 22 | Example 23 | Example 24 | Example 25 | Example 26 |
|---|---|---|---|---|---|---|
| L-ascorbic acid (mg) | - | 0.4 | - | - | - | - |
| Sodium bisulfite (mg) | - | - | 0.4 | - | - | - |
| Propyl gallate (mg) | - | - | - | 0.4 | - | - |
| Dibutylhydroxytoluene (mg) | - | - | - | - | 0.4 | - |
| Tocopherol (mg) | - | - | - | - | - | 0.4 |
| Weight ratio of antioxidant per anhydrous dasatinib | - | 0.02 | 0.02 | 0.02 | 0.02 | 0.02 |
| ΔE value | 8.8 | 8.75 | 7.01 | 5.57 | 2.26 | 3.11 |
| Total related substances (%) | 0.77 | 0.41 | 0.41 | 0.44 | 0.5 | 0.36 |

ANHYDROUS DASATINIB-CONTAINING PREPARATION

CROSS-REFERENCE TO RELATED APPLICATIONS

This application is based upon and claims the benefit of priority from the prior Japanese Patent Application No. 2017-224570, filed on Nov. 22, 2017, and PCT Application No. PCT/JP2018/042968, filed on Nov. 21, 2018, the entire contents of which are incorporated herein by reference.

FIELD

The present invention relates to an anhydrous dasatinib-containing preparation. Specifically, it relates to the anhydrous dasatinib-containing preparation with improved photostability during storage. In the description, "anhydrous dasatinib-containing preparation" includes an anhydrous dasatinib-containing pharmaceutical composition, and an anhydrous dasatinib-containing tablet.

BACKGROUND

A dasatinib competes with ATP at the ATP-binding site in the kinase domain of certain protein tyrosine kinases and inhibits not only BCR-ABL but also SRC-family kinases (SRC, LCK, YES, FYN), c-KIT, EPH (ephrin) A2 receptor and PDGF (platelet-derived growth factor) β receptor. Due to this inhibitory effect, the dasatinib has been described in Japanese laid-open patent publication No. 2008-540440 and pharmaceutical product interview form of SPRYCEL tablet created August 2016 (Revision 11th Edition) for its indication in chronic myeloid leukemia, relapsed or refractory Philadelphia chromosome-positive acute lymphocytic leukemia.

Pharmaceutical product interview form of SPRYCEL tablet created August 2016 (Revision 11th Edition) describes that no changes were observed in the stability of a dasatinib hydrate under various conditions as a result of stress testing in which light (1.2 million Lux·hr as total illumination and 200 W·hr/m$^2$ as total near-ultraviolet radiation energy) equivalent to the light exposure set out in the photostability guideline was exposed.

In addition, Japanese Patent No. 6081763 describes an anhydrous dasatinib crystal and a preparation containing the anhydrous dasatinib crystal, in place of a dasatinib hydrate. However, the photostability of the anhydrous dasatinib was not investigated in the Japanese Patent No. 6081763.

SUMMARY

As a result of studies, the inventors revealed that the dasatinib-containing preparation was unstable to light and in particular, the preparation containing anhydrous dasatinib as a drug substance was unstable to light.

One of the aims in the present invention is to provide the anhydrous dasatinib-containing preparation with improved photostability upon storage.

According to one embodiment of the present invention, the anhydrous dasatinib-containing preparation comprising an anhydrous dasatinib and a titanium oxide or colorant or antioxidant is provided.

The weight ratio of the titanium oxide per the anhydrous dasatinib may be more than 0 and 2 or less, or the weight ratio of the colorant per the anhydrous dasatinib may be more than 0 and 1 or less, or the weight ratio of the antioxidant per the anhydrous dasatinib may be more than 0 and 0.5 or less.

The colorant may be a yellow ferric oxide or a red ferric oxide.

The antioxidant may be an antioxidant with a benzene ring.

The antioxidant with a benzene ring may be a tocopherol or a dibutylhydroxytoluene.

According to one embodiment of the present invention, the anhydrous dasatinib-containing preparation is provided, characterized by having a film-coating part containing a titanium oxide or a colorant outside an uncoated tablet containing the anhydrous dasatinib.

The weight ratio of the titanium oxide per the anhydrous dasatinib may be more than 0 and 2 or less, or the weight ratio of the colorant per anhydrous dasatinib may be more than 0 and 1 or less.

The colorant may be the yellow ferric oxide or the red ferric oxide.

BRIEF DESCRIPTION OF DRAWINGS

FIG. 1 is a diagram showing pharmaceutical properties, etc. of anhydrous dasatinib-containing tablets according to examples of the present invention;

FIG. 2 is a diagram showing the pharmaceutical properties, etc. of anhydrous dasatinib-containing pharmaceutical compositions according to examples of the present invention;

FIG. 3 is a diagram showing the pharmaceutical properties, etc. of anhydrous dasatinib-containing tablets according to examples of the present invention;

FIG. 4 is a diagram showing the pharmaceutical properties, etc. of anhydrous dasatinib-containing pharmaceutical compositions according to examples of the present invention; and FIG. 5 is a diagram showing the pharmaceutical properties, etc. of anhydrous dasatinib-containing pharmaceutical compositions according to examples of the present invention.

DESCRIPTION OF EMBODIMENTS

An anhydrous dasatinib-containing preparation according to the present invention is described below. However, the anhydrous dasatinib-containing preparation of the present invention is not interpreted only in terms of the embodiments and examples described below.

Previously, it was not known that the anhydrous dasatinib-containing preparation was unstable to light, and light-induced discoloration or the generation of related substances. The present inventors found for the first time that the anhydrous dasatinib-containing preparation is unstable to light.

The present inventors have investigated a variety of additives to improve the photostability of the anhydrous dasatinib-containing preparation, as also shown in the examples described below. As a result, it was newly found that adding the titanium oxide or colorants or antioxidants could improve the photostability of the anhydrous dasatinib-containing preparation and inhibit light-induced discoloration and generation of related substances.

The anhydrous dasatinib-containing preparation of the present invention contains the anhydrous dasatinib and the titanium oxide. In one embodiment, the anhydrous dasatinib-containing preparation comprises a predetermined amount of the anhydrous dasatinib, and in the form of a tablet, the content of the anhydrous dasatinib is, for example, 20 mg/tablet or 50 mg/tablet.

In one embodiment, it is preferable that the weight ratio of the titanium oxide to be added to the anhydrous dasatinib-containing preparation per anhydrous dasatinib is more than 0 and 2 or less, and the range is 0.0075 or more and 0.2 or less.

The anhydrous dasatinib-containing preparation of the present invention also contains the anhydrous dasatinib and the colorant. The colorant such as the yellow ferric oxide, the red ferric oxide, black iron oxide, edible yellow No. 5, edible yellow No. 5 aluminum lake, riboflavin, etc. may be used. In particular, the yellow ferric oxide, the red ferric oxide can be used preferentially. These colorants can be used alone or in combination with more than one species.

In one embodiment, it is preferable that the weight ratio of the colorant to be added to the anhydrous dasatinib-containing preparation per anhydrous dasatinib is more than 0 and 1 or less, and the range is 0.0005 or more and 0.08 or less.

In addition, the anhydrous dasatinib-containing preparation of the present invention contains the anhydrous dasatinib and the antioxidant. For example, tocopherol, dibutyl-hydroxytoluene, propyl gallate, sodium bisulfite, ascorbic acid, sodium ascorbate, butylhydroxyanisole, nordihydroguaiaretic acid, erythorbic acid, sodium erythorbate, sodium pyrosulfite, Rongalit, etc. may be used as the antioxidants. In particular, tocopherols, dibutylhydroxytoluene, propyl gallate, sodium bisulfite, and ascorbic acid can be used preferentially. Notably, tocopherols, dibutylhydroxytoluene can be used even more preferably.

In one embodiment, it is preferable that the weight ratio of the antioxidant added to the anhydrous dasatinib-containing preparation per anhydrous dasatinib is more than 0 and 0.5 or less, and the weight ranges from 0.0001 or more to 0.02 or less.

In one embodiment, the anhydrous dasatinib-containing preparation may be a pharmaceutical composition of the powder and may be a tablet. The anhydrous dasatinib-containing tablet may also be an uncoated tablet or film-coated to be a film-coated tablet.

When the anhydrous dasatinib-containing tablet is the uncoated tablet, the titanium oxide or the colorant or the antioxidant with the benzene ring is contained in the same uncoated tablet part as the anhydrous dasatinib. The anhydrous dasatinib-containing tablet may also have an additional film-coating part which is known on the uncoated tablet.

In cases where the anhydrous dasatinib-containing tablet is the film-coated tablet, the titanium oxide or the colorant can contain some or all of them in the film-coating part. In this case, the uncoated tablet part may contain the titanium oxide, the colorant, the antioxidant alone or two or more.

The anhydrous dasatinib-containing preparation of one embodiment may additionally include additives such as excipients, binders, disintegrants, emulsifiers, stabilizers, flavoring agents, plasticizers, lubricants, etc.

As the excipients sugar derivatives, starch derivatives, cellulose derivatives, gum arabic, dextran, pullulan, silicate derivatives, phosphates, carbonates and sulfates, etc can be used. As the sugar derivatives, for example, lactose, sucrose, glucose, mannitol, erythritol, trehalose, maltose, xylitol, sorbitol etc. can be used. As the starch derivatives, for example, corn starch, potato starch, α-starch, dextrin, etc. can be used. As the cellulose derivatives, for example, crystalline cellulose, etc. can be used. As the silicate derivatives, for example, light anhydrous silicic acid, synthetic aluminum silicate, calcium silicate, magnesium metasilicate, etc. can be used. As the phosphate, for example, calcium hydrogen phosphate, etc. can be used. As the carbonate, for example, calcium carbonate, magnesium carbonate, sodium bicarbonate, etc. can be used. As the sulfates, for example, calcium sulfate, etc. can be used. These excipients can be used alone or in a combination of more than one species.

As disintegrants, for example, crospovidone, carmellose calcium, carmellose sodium, croscarmellose sodium, carmellose, crosslinked polyvinylpyrrolidone, low substituted hydroxypropylcellulose, starches, etc. can be used. These disintegrants can be used alone or in combination of more than one species.

As the binders, for example, hydroxypropylcellulose, hydroxypropylmethylcellulose, polyvinylpyrrolidone, polyvinyl alcohol, macrogol and compounds shown above as excipients can be used. These binders can be used alone or in a combination of more than one species.

As the emulsifiers, for example, colloidal clays, metal hydroxides, anionic surfactants, cationic surfactants and non-ionic surfactants can be used. As the colloidal clays, for example, bentonite, VEEGUM, etc. can be used. As metal hydroxides, for example, magnesium hydroxide, aluminum hydroxide, etc. can be used. As the anionic surfactants, for example, sodium lauryl sulfate can be used. As cationic surfactants, for example, benzalkonium chloride, etc. can be used. As the non-ionic surfactants, for example, polyoxyethylene alkyl ethers, polyoxyethylene sorbitan fatty acid esters, sucrose fatty acid esters, and the like can be used. These emulsifiers can be used alone or in a combination of more than one species.

As the stabilizers, for example, parahydroxybenzoate esters, alcohols, phenols, thimerosal, dehydroacetic acid, sorbic acid, and the like can be used. As the parahydroxybenzoate esters, for example, methylparaben, propylparaben, etc. can be used. As the alcohols, for example, chlorobutanol, benzyl alcohol, phenylethyl alcohol, etc. can be used. These stabilizers can be used alone or in a combination of more than one species.

As the flavoring agents, for example, sweeteners, acidifiers and flavorings can be used. As the sweeteners, for example, saccharin sodium, sucralose, thaumatin, acesulfame potassium, stevia extract, sucrose, aspartame, etc. can be used. As the acidifiers for example, citric acid, malic acid, tartaric acid, etc. can be used. As flavoring agents, for example, menthol, lemon extract, orange extract, etc. can be used as flavoring agents. These flavoring agents can be used alone or in a combination of two or more.

As the plasticizers, for example, triethyl citrate, glycerin fatty acid ester, triacetin, propylene glycol, macrogol, glyceryl monostearate, and the like can be used. These plasticizers can be used alone or in a combination of more than one species.

As the lubricants, for example, stearic acid, metal stearate (calcium stearate, magnesium stearate, etc.), talc, colloidal silica, waxes (bead wax, gay wax, etc.), boric acid, adipic acid, sulfate (sodium sulfate, etc.), glycol, fumarate, sodium stearyl fumarate, sodium benzoate, D,L-leucine, lauryl sulfate (sodium lauryl sulfate, magnesium lauryl sulfate, etc.), silicic acids (silicic anhydride, silicic acid hydrate, etc.) and compounds shown above as excipients can be used. These lubricants may be used alone or in a combination of two or more.

The anhydrous dasatinib-containing preparation according to the present invention can improve photostability during storage by adding the titanium oxide or colorants or antioxidants, etc. In addition, the anhydrous dasatinib-containing preparation of the present invention can improve the photostability of anhydrous dasatinib contained in the uncoated tablet during storage by making a film-coated tablet containing the titanium oxide or colorants etc. in the film-coating part.

(Manufacturing Method)

The anhydrous dasatinib-containing preparation of the present invention can be manufactured according to the known manufacturing methods in the pharmaceutical field. For example, fluidized bed granulation or rotating fluidized bed granulation is performed while spraying solutions to an anhydrous dasatinib and, if appropriate, mixtures containing the various additives, etc. mentioned above. A commercial machine such as MP-01 (manufactured by Powrex Corporation) and FLO-5 (manufactured by Freund Corporation) can be used as a fluid bed granulator. MP-01 (manufactured by Powrex Corporation) can also be used as a rolling fluid bed granulator. Separately, granulation can be performed using a high-speed stirring kneader, "FS-GS-5J" (manufactured by Fukae Kogyo Co., Ltd.) or the like can be used. Granules obtained in the wet granulation process should be dried and particle size regulated, then mixed with disintegrators, lubricants, and, if necessary, various additives described above. The mixed compositions can be tableted to obtain the anhydrous dasatinib-containing preparation according to one embodiment. Film-coating can be performed on the resulting uncoated tablet to obtain the anhydrous dasatinib-containing tablet according to one embodiment. Commercial machines such as HC-LABO (made by Freund Corporation) can be used as film-coating devices. In one embodiment, any of the above additives may be mixed into a granulation material and shaped following a wet granulation process.

(Color Change)

Using a spectral color contrast meter (NIPPON DENSHOKU INDUSTRIES CO., LTD., Model: SE-6000), the color change ΔE value of the preparation irradiated with 10000Lux./hr of light for 5 days was measured based on the color tone of the preparation immediately after manufacturing, and the mean value of the measurement value of 5 tablets was calculated.

(Total Related Substances)

In the description, the purities of the anhydrous dasatinib were evaluated using liquid chromatography as an assessment of the stability. The ratio of the peak area of related substances derived from the anhydrous dasatinib to that of the anhydrous dasatinib was calculated to determine the total related substances (%).

EXAMPLES

Specific examples and test results of the anhydrous dasatinib-containing preparation described above are provided and explained in more detail.

Example 1

Anhydrous dasatinib 20.0 mg, lactose hydrate (Pharmatose200M, DMV) 27.0 mg, crystalline cellulose (UF-711, Asahi Kasei Chemicals) 15.0 mg, croscarmellose sodium (Ac-Di-Sol, FMC) 1.6 mg, and hydroxypropylcellulose (HPC-L,NIPPON SODA) 2.4 mg were put into and mixed in a high-speed stirring mixer (FS-GS-5J, Fukae Kogyo Co., Ltd.). After mixing, the purified water was fed and kneaded so that the solid-liquid ratio was 35%. The kneaded product was sieved through sieve No. 8 and then put into a flow-bed granulation drier (MP-01, Powrex Corporation) to be dried. Dried products were placed in a grain preparation machine (P-04-S, Dalton) and particle size regulated. Crystalline cellulose (PH-102, Asahi Kasei Chemicals) 12.0 mg, croscarmellose sodium (Ac-Di-Sol, FMC) 1.6 mg, and magnesium stearate (Taihei Chemical) 0.4 mg were mixed as a formulation ratio with the sized product to prepare a tableting mixture.

Using a tablet press (VELAS, KIKUSUI SEISAKUSHO), a tableting mixture was compressed to a weight of 80 mg to obtain an uncoated tablet. Further, Hypromellose (TC-5M, Shinetsu Chemical) 2.6 mg, hydroxypropylcellulose (HPC-SL, NIPPON SODA) 0.3 mg, titanium oxide (NA-61, Toho Titanium) 0.3 mg as a formulation ratio were dissolved and dispersed in purified water with the amount to be 8.5% of hypromellose to obtain a composition for film coating. The uncoated tablet were coated with the composition for film coating so as to a predetermined weights using a coating machine (HC-LABO20, Freund Corporation), and a small amount of carnauba wax (polishing wax 105, NIPPON WAX) was added as a shining agent to obtain 83.2 mg of the anhydrous dasatinib-containing tablet in Example 1.

Example 2

In Example 1, the titanium oxide having a weight ratio of 0.015 per the anhydrous dasatinib was mixed in the film-coating part, whereas in Example 2, the titanium oxide having a weight ratio of 0.03 per the anhydrous dasatinib was mixed in the film-coating part. Except for this, as in Example 1, 83.2 mg of the anhydrous dasatinib-containing tablet was obtained.

Example 3

In Example 1, a weight ratio of the 0.015 titanium oxide per the anhydrous dasatinib was mixed in the film-coating part, whereas in Example 3, the titanium oxide having a weight ratio of the 0.045 per the anhydrous dasatinib was mixed in the film-coating part. Except for this, as in Example 1, 83.2 mg of the anhydrous dasatinib-containing tablet was obtained.

Example 4

In Example 1, the coating was performed so that the total of the film-coating part was 3.2 mg, whereas in Example 4, the coating was performed so that the total of the film-coating part was 1.6 mg. Further, in Example 1, the titanium oxide having a weight ratio of 0.015 per the anhydrous dasatinib was mixed in the film-coating part, whereas in Example 4, titanium oxide having a weight ratio of 0.0075 per the anhydrous dasatinib was mixed in the film-coating part. Except for this, as in Example 1, 81.6 mg of the anhydrous dasatinib-containing tablet was obtained.

Example 5

In Example 4, the titanium oxide having a weight ratio of 0.0075 per the anhydrous dasatinib was mixed in the film-coating part, whereas in Example 5, titanium oxide having a weight ratio of 0.015 per the anhydrous dasatinib was mixed in the film-coating part. Except for this, as in Example 4, 81.6 mg of the anhydrous dasatinib-containing tablet was obtained.

Example 6

In Example 4, the titanium oxide having a weight ratio of 0.0075 per the anhydrous dasatinib was mixed in the film-coating part, whereas in Example 6, titanium oxide having a weight ratio of 0.0225 per the anhydrous dasatinib was mixed in the film-coating part. Except for this, as in Example 4, 81.6 mg of the anhydrous dasatinib-containing tablet was obtained.

Example 7

In Example 1, the coating was performed so that the total of the film-coating part was 3.2 mg, whereas in Example 7, the coating was performed so that the total of the film-coating part was 2.4 mg. Further, in Example 1, the titanium oxide having a weight ratio of 0.015 per the anhydrous dasatinib was mixed, whereas in Example 7, titanium oxide having a weight ratio of 0.01125 per the anhydrous dasatinib was mixed in the film-coating part. Except for this, as in Example 1, 82.4 mg of the anhydrous dasatinib-containing tablet was obtained.

Example 8

In Example 7, titanium oxide having the weight ratio of 0.01125 per the anhydrous dasatinib was mixed in the film-coating part, whereas in Example 8, titanium oxide having a weight ratio of 0.0225 per the anhydrous dasatinib was mixed in the film-coating part. Except for this, as in Example 7, 82.4 mg of the anhydrous dasatinib-containing tablet was obtained.

Example 9

In Example 7, the titanium oxide having a weight ratio of 0.01125 per the anhydrous dasatinib was mixed in the film-coating part, whereas in Example 9, titanium oxide having a weight ratio of 0.03375 per the anhydrous dasatinib was mixed in the film-coating part. Except for this, as in Example 7, 82.4 mg of the anhydrous dasatinib-containing tablet was obtained.

Example 10

The anhydrous dasatinib 20.0 mg, lactose hydrate (Pharmatose (registered trademark) 200M, DMV) 27.0 mg, crystalline cellulose (UF-711, Asahi Kasei Chemicals) 15.0 mg, croscarmellose sodium (Ac-Di-Sol, FMC) 1.6 mg, and hydroxypropylcellulose (HPC-L, NIPPON SODA) 2.4 mg were put into and mixed in a high-speed stirring mixer (FS-25, Fukae Kogyo Co., Ltd.) as the formulation ratio. After mixing, the purified water was fed and kneaded so that the solid-liquid ratio was 35%. The kneaded product was sieved through sieve No. 8 and then put into a fluidized bed granulation dryer (FLO-5, Freund Corporation) to be dried. Dried products were placed in a grain preparation machine (P-04-S, Dalton) and particle size regulated. Crystalline cellulose (PH-102, Asahi Kasei Chemicals) 12.0 mg, croscarmellose sodium (Ac-Di-Sol, FMC) 1.6 mg, and magnesium stearate (Taihei Chemical) 0.4 mg were mixed as a formulation ratio with the sized product. In addition, titanium oxide (NA-61, Toho Titanium) was added to this mixture at a formulation ratio of 0.4 mg to obtain 80.4 mg of the pharmaceutical composition containing anhydrous dasatinib in Example 10.

Example 11

In Example 10, the titanium oxide having a weight ratio of 0.02 per the anhydrous dasatinib was mixed, whereas in Example 11, titanium oxide having a weight ratio of 0.04 per the anhydrous dasatinib was mixed. Except for this, as in Example 10, 80.8 mg of the pharmaceutical composition containing anhydrous dasatinib was obtained.

Example 12

In Example 10, the titanium oxide having a weight ratio of 0.02 per the anhydrous dasatinib was mixed, whereas in Example 12, titanium oxide having a weight ratio of 0.12 per the anhydrous dasatinib was mixed. Except for this, as in Example 10, 82.4 mg of the pharmaceutical composition containing anhydrous dasatinib was obtained.

Example 13

In Example 10, the titanium oxide having a weight ratio of 0.02 per the anhydrous dasatinib was mixed, whereas in Example 13, titanium oxide having a weight ratio of 0.20 per the anhydrous dasatinib was mixed. Except for this, as in Example 10, 84.0 mg of the pharmaceutical composition containing anhydrous dasatinib was obtained.

Example 14

In Example 1, the anhydrous dasatinib was mixed with 20 mg in the uncoated tablet part, but in Example 14, the anhydrous dasatinib was also mixed with 20 mg in the uncoated tablet part. In Example 1, the titanium oxide having a weight ratio of 0.015 per the anhydrous dasatinib was mixed, whereas in Example 14, red ferric oxide having a weight ratio of 0.0005 per the anhydrous dasatinib was mixed. Except for this, as in Example 11, 83.21 mg of the anhydrous dasatinib-containing tablet was obtained.

Example 15

In Example 14, the red ferric oxide having a weight ratio of 0.0005 per the anhydrous dasatinib was mixed, whereas in Example 15, red ferric oxide having a weight ratio of 0.005 per the anhydrous dasatinib was mixed. Except for this, as in Example 14, 83.3 mg of the anhydrous dasatinib-containing tablet was obtained.

Example 16

In Example 10, the titanium oxide having a weight ratio of 0.02 per the anhydrous dasatinib was mixed, whereas in Example 16, yellow ferric oxide having a weight ratio of 0.02 per the anhydrous dasatinib was mixed. Except for this, as in Example 10, 80.4 mg of the pharmaceutical composition containing anhydrous dasatinib was obtained.

Example 17

In Example 16, yellow ferric oxide having a weight ratio of 0.02 per the anhydrous dasatinib was mixed, whereas in Example 17, yellow ferric oxide having a weight ratio of 0.04 per the anhydrous dasatinib was mixed. Except for this, as in Example 16, 80.8 mg of the pharmaceutical composition containing anhydrous dasatinib was obtained.

Example 18

In Example 16, yellow ferric oxide having a weight ratio of 0.02 per the anhydrous dasatinib was mixed, whereas in Example 18, yellow ferric oxide having a weight ratio of 0.08 per the anhydrous dasatinib was mixed. Except for this, as in Example 16, 81.6 mg of the pharmaceutical composition containing anhydrous dasatinib was obtained.

Example 19

In Example 16, yellow ferric oxide having a weight ratio of 0.02 per the anhydrous dasatinib was mixed, whereas in Example 19, red ferric oxide having a weight ratio of 0.02 per the anhydrous dasatinib was mixed. Except for this, as in Example 16, 80.4 mg of the pharmaceutical composition containing anhydrous dasatinib was obtained.

Example 20

In Example 19, red ferric oxide having a weight ratio of 0.02 per the anhydrous dasatinib was mixed, whereas in Example 20, red ferric oxide having a weight ratio of 0.04 per the anhydrous dasatinib was mixed. Except for this, as in Example 19, 80.8 mg of the pharmaceutical composition containing anhydrous dasatinib was obtained.

Example 21

In Example 19, red ferric oxide having a weight ratio of 0.02 per the anhydrous dasatinib was mixed, whereas in Example 21, red ferric oxide having a weight ratio of 0.08 per the anhydrous dasatinib was mixed. Except for this, as in Example 19, 81.6 mg of the pharmaceutical composition containing anhydrous dasatinib was obtained.

Example 22

In Example 10, titanium oxide having a weight ratio of 0.02 per the anhydrous dasatinib was mixed, whereas in Example 22, L-ascorbic acid having a weight ratio of 0.02 per the anhydrous dasatinib was mixed. Except for this, as in Example 10, 80.4 mg of the pharmaceutical composition containing anhydrous dasatinib was obtained.

Example 23

In Example 22, L-ascorbic acid having a weight ratio of 0.02 per the anhydrous dasatinib was mixed, whereas in Example 23, sodium bisulfite having a weight ratio of 0.02 per the anhydrous dasatinib was mixed. Except for this, as in Example 22, 80.4 mg of the pharmaceutical composition containing anhydrous dasatinib was obtained.

Example 24

In Example 22, L-ascorbic acid having a weight ratio of 0.02 per the anhydrous dasatinib was mixed, whereas in Example 24, propyl gallate having a weight ratio of 0.02 per the anhydrous dasatinib was mixed. Except for this, as in Example 22, 80.4 mg of the pharmaceutical composition containing anhydrous dasatinib was obtained.

Example 25

In Example 22, L-ascorbic acid having a weight ratio of 0.02 per the anhydrous dasatinib was mixed, whereas in Example 25, dibutylhydroxytoluene having a weight ratio of 0.02 per the anhydrous dasatinib was mixed. Except for this, as in Example 22, 80.4 mg of the pharmaceutical composition containing anhydrous dasatinib was obtained.

Example 26

In Example 22, L-ascorbic acid having a weight ratio of 0.02 per the anhydrous dasatinib was mixed, whereas in Example 26, tocopherol having a weight ratio of 0.02 per the anhydrous dasatinib was mixed. Except for this, as in Example 22, 80.4 mg of the pharmaceutical composition containing anhydrous dasatinib was obtained.

Comparative Example 1

Comparative Example 1 is the anhydrous dasatinib drug substance.

Comparative Example 2

In Example 1, a film coating was applied to the uncoated tablet part, but in Example 2, the anhydrous dasatinib-containing tablet 80.0 mg was obtained in the same manner as in Example 1, except that only the uncoated tablet part without the film coating was applied.

Comparative Example 3

In Example 1, the titanium oxide having a weight ratio of 0.02 per the anhydrous dasatinib was mixed in the film-coating part, whereas in Comparative Example 3, titanium oxide was not mixed in the film-coating part. Except for this, as in Example 10, 80.8 mg of the anhydrous dasatinib-containing tablet was obtained.

Comparative Example 4

In Example 10, the titanium oxide having a weight ratio of 0.02 per the anhydrous dasatinib was mixed, whereas in Comparative Example 4, titanium oxide was not mixed. Except for this, as in Example 10, 80.0 mg of the pharmaceutical composition containing anhydrous dasatinib was obtained.

FIG. 1 shows the physical properties, etc. of the preparation of the anhydrous dasatinib-containing tablet according to the example of the present invention. In the anhydrous dasatinib-containing tablet having the film-coating part, the amount of the film-coating part and the percentage of the titanium oxide in the film-coating part were varied, respectively, and the color change (ΔE) and the total related substances (%) of the preparations irradiated with 10000 Lux./hr of light for 5 days were determined, respectively.

(Color Change)

For color change, the ΔE value of the amount of color change was measured using a spectral color contrast meter (NIPPON DENSHOKU INDUSTRIES CO., LTD., Model: SE-6000) based on the color tone of the drug product immediately after manufacturing, and the mean value of the measured value of 5 tablets was calculated.

(Total Related Substances)

For the total related substances, the purities of the anhydrous dasatinib were evaluated using liquid chromatography as shown below. The ratio of the peak area of the related substances derived from the anhydrous dasatinib to that of the anhydrous dasatinib was calculated to determine the total related substances (%). Specifically, a column was octadecylsilated silica gels (particle size, 5 μm; column inner diameter, 4.6 mm; column length, 250 mm; GL Sciences), mobile phase A was 0.01 M aqueous potassium dihydrogen phosphate solution, mobile phase B was acetonitrile, and the detector was ultraviolet absorbance spectrophotometer (measured wavelength: 230 nm), respectively. The temperature of the column was set at a constant temperature around 40° C., with a flow rate of 0.5 mL/min and an injection volume of 10 μL. A mixed ratio (A/B) with the mobile phases A and B was set as follows for the delivery of the mobile phase after injecting the samples. A/B was set as a concentration gradient of 90/10 to 60/40 for 0 to 15 min after infusion. The concentration gradient of A/B was set at 60/40 to 40/60 for 15 to 35 minutes. The concentration gradient of A/B was set at 40/60 to 20/80 for 35 to 40 minutes. The concentration gradient of A/B was set at 20/80 for 40 to 45 min. The concentration gradient of A/B was 20/80 to 90/10 for 45 to 48 minutes. From 48 to 50 min, A/B was set as the concentration gradient of 90/10.

The ΔE was 18.56 and the total related substances (%) was 0.51 in Comparative Example 1, which was the anhydrous dasatinib drug substance. The ΔE value was 20.38 and the total related substance (%) was 0.4 in Comparative Example 2, which was the anhydrous dasatinib tablet without the film-coating part. These results indicate that the anhydrous dasatinib drug and the anhydrous dasatinib tablet that does not have the film-coating part are associated with increased coloration and related substances.

Compared with Comparative Example 3 having the film-coating part, Example 1 having the film-coating part containing 0.015 of the weight ratio of the titanium oxide per the anhydrous dasatinib had smaller ΔE values and total related substances (%), and improved color change and production of related substances. Compared to Example 1, Examples 2 and 3, in which the compounding proportion of the titanium oxide increased, the color change and the generation of the related substances were more improved as the compounding proportion of the titanium oxide in the film-coating part increased, as the ΔE value and the total related substances (%) became even smaller.

Compared with Comparative Example 3 having the film-coating part, Example 4 having the film-coating part mixed with the titanium oxide at a weight ratio of 0.0075 per the anhydrous dasatinib, Example 7 having the film-coating part mixed with the titanium oxide at a weight ratio of 0.01125, as in Example 1, the ΔE value and total related substances (%) were reduced, resulting in improved color change and generation of the related substances. In Examples 4 to 6 and Examples 7 to 9, same as in Examples 1 to 3, as the proportion of the titanium oxide in the film-coating part increases, the ΔE value and the total related substance (%) become smaller, the color change and the generation of related substances were improved more.

FIG. 2 shows the pharmaceutical properties, etc. of the anhydrous dasatinib-containing pharmaceutical compositions according to the example of the present invention. Unlike the anhydrous dasatinib-containing tablet containing the titanium oxide in the film-coating part shown in FIG. 1, the anhydrous dasatinib-containing pharmaceutical composition was used to determine the color change (ΔE) and total related substances (%) by varying the percentage of the titanium oxide.

Compared with Comparative Example 4, Example 10, in which the titanium oxide was mixed with the weight ratio of 0.02 per anhydrous dasatinib had smaller ΔE values and total related substances (%), resulting in improved color change and production of related substances.

Compared to Example 10, Examples 11 to 13, in which the compounding ratio of the titanium oxide increased, the ΔE value and total related substances (%) became smaller as the compounding ratio of the titanium oxide in the anhydrous dasatinib-containing pharmaceutical compositions increased, so that the color change and the formation of related substances were improved more.

Thus, the addition of the titanium oxide to the film-coating part of the anhydrous dasatinib-containing tablet or to the pharmaceutical composition containing anhydrous dasatinib inhibited the color change of the anhydrous dasatinib and the formation of related substances, thereby improving photostability during storage.

FIG. 3 shows the pharmaceutical properties, etc. of the anhydrous dasatinib-containing tablet according to the example of the present invention. Unlike the anhydrous dasatinib-containing tablet mixed with the titanium oxide in the film coating part shown in FIG. 1, the percentage of the red ferric oxide in the film-coating part was changed to determine the color change (ΔE) and total related substances (%), respectively, in the anhydrous dasatinib-containing tablet having the film-coating part.

Compared with Comparative Example 3 having the film-coating part, Example 14 having the film-coating part mixed with the red ferric oxide at a ratio of 0.0005 per the anhydrous dasatinib had smaller ΔE values and total related substances (%), and improved color change and production of related substances. Compared with Example 14, Example 15, in which the proportion of the red ferric oxide was increased, the ΔE value and the total related substance (%) became even smaller, and the color change and the production of related substances were improved as the proportion of the red ferric oxide in the film-coating part increased.

FIG. 4 shows the pharmaceutical properties, etc. of the anhydrous dasatinib-containing pharmaceutical compositions according to the example of the invention. Unlike the anhydrous dasatinib-containing tablet containing the red ferric oxide in the film-coating part shown in FIG. 3, the percentage of the yellow ferric oxide or the red ferric oxide in the anhydrous dasatinib-containing pharmaceutical composition was varied to determine the color change (ΔE) and the total related substance (%).

Compared with Comparative Example 4, Example 16 mixed with yellow ferric oxide having a weight ratio of 0.02 per the anhydrous dasatinib showed smaller ΔE values and total related substances (%), and improved color change and production of related substances.

Compared to Example 16, in Examples 17 and 18 in which the proportion of the yellow ferric oxide was increased, the ΔE values and total related substances (%) further reduced, and as increasing the proportion of the yellow ferric oxide in the anhydrous dasatinib-containing pharmaceutical compositions, the color changes and the formation of related substances improved. Examples 19 to 21 in which the yellow ferric oxide was replaced with the red ferric oxide, as in Examples 16 to 18, the ΔE values and total related substances (%) decreased as the percentage of the red ferric oxide in the anhydrous dasatinib-containing pharmaceutical compositions increased, and the color change and the production of related substances improved more.

Thus, by mixing the yellow ferric oxide or the red ferric oxide to the film-coating part of the anhydrous dasatinib-containing tablet or to the anhydrous dasatinib-containing pharmaceutical composition inhibited the color change of the anhydrous dasatinib and the formation of related substances, thereby improving photostability during storage.

FIG. 5 shows the pharmaceutical properties, etc. of the anhydrous dasatinib-containing pharmaceutical composition according to the example of the present invention. Different from the anhydrous dasatinib-containing pharmaceutical compositions with the yellow ferric oxide or the red ferric oxide as shown in FIG. 4, the anhydrous dasatinib-containing pharmaceutical compositions mixed with the antioxidant were used to measure the color change (ΔE) and the total related substances (%), respectively, by varying the type of the antioxidant.

The percentage of the antioxidant was 0.02 per the weight ratio of anhydrous dasatinib.

Compared with Comparative Example 4, Example 22 mixed with L-ascorbic acid and Example 23 mixed with sodium bisulfite both resulted in fewer total related substances (%), thus improving the generation of related substances. In Example 24, where propyl gallate was mixed, the ΔE value was also reduced, so not only the production of related substances was improved, but also the color change was improved. In addition, Example 25, in which dibutylhydroxytoluene was mixed, and Example 26, in which tocopherol was mixed, had a very small ΔE value and very low total related substances (%), resulting in a more improved color change and generation of related substances.

Thus, by mixing the antioxidants with the anhydrous dasatinib-containing pharmaceutical compositions, the production of related substances can be inhibited and photostability during storage can be improved. Dibutylhydroxytoluene or tocopherol can also inhibit the color change of the anhydrous dasatinib and further improve photostability during storage.

As explained above, the anhydrous dasatinib-containing preparation of the present invention can improve the photostability during storage by containing the anhydrous dasatinib and the titanium oxide or colorants or antioxidants.

According to the present invention, an anhydrous dasatinib-containing preparation with improved photostability upon storage is provided.

What is claimed is:

1. An anhydrous dasatinib-containing uncoated tablet, comprising:
    an anhydrous dasatinib; and
    a titanium oxide or a colorant or an antioxidant,
    wherein;
    a weight ratio of the titanium oxide per the anhydrous dasatinib ranges from 0.0075 to 2;
    a weight ratio of the colorant per the anhydrous dasatinib ranges from 0.0005 to 1; or
    a weight ration of the antioxidant per the anhydrous dasatinib ranges from 0.0001 to 0.5.

2. The anhydrous dasatinib-containing preparation according to claim 1,
    wherein;
    the colorant is a yellow ferric oxide or a red ferric oxide.

3. A film-coated tablet containing anhydrous dasatinib, comprising:
    an uncoated tablet including an anhydrous dasatinib; and
    a film-coating part formed outside of the uncoated tablet, the film-coating part including a titanium oxide or a colorant,
    wherein;
    a weight ratio of the titanium oxide per the anhydrous dasatinib ranges from 0.0075 to 2; or
    a weight ratio of the colorant per the anhydrous dasatinib ranges from 0.0005 to 1.

4. The anhydrous dasatinib-containing preparation according to claim 3,
    wherein;
    the colorant is a yellow ferric oxide or a red ferric oxide.

* * * * *